(12) United States Patent
McGall (10) Patent No.: US 11,149,301 B2
(45) Date of Patent: Oct. 19, 2021

(54) PREPARATION OF UNIVERSAL SPIN-COATABLE AMINE-REACTIVE SURFACE COATINGS FOR BIOMOLECULE ARRAY FABRICATION

(71) Applicant: CENTRILLION TECHNOLOGY HOLDINGS CORPORATION, Grand Cayman (KY)

(72) Inventor: Glenn McGall, Palo Alto, CA (US)

(73) Assignee: CENTRILLION TECHNOLOGY HOLDINGS CORPORATION, Grand Cayman (KY)

(*) Notice: Subject to any disclaimer, the term of this patent is extended or adjusted under 35 U.S.C. 154(b) by 199 days.

(21) Appl. No.: 16/492,891

(22) PCT Filed: Mar. 6, 2018

(86) PCT No.: PCT/US2018/021036
§ 371 (c)(1),
(2) Date: Sep. 10, 2019

(87) PCT Pub. No.: WO2018/169725
PCT Pub. Date: Sep. 20, 2018

(65) Prior Publication Data
US 2020/0071752 A1    Mar. 5, 2020

Related U.S. Application Data

(60) Provisional application No. 62/472,680, filed on Mar. 17, 2017.

(51) Int. Cl.
*C07H 21/04* (2006.01)
*C12Q 1/6837* (2018.01)
(Continued)

(52) U.S. Cl.
CPC ........... *C12Q 1/6837* (2013.01); *B05D 1/005* (2013.01); *B05D 1/38* (2013.01); *B05D 3/02* (2013.01); *B05D 3/108* (2013.01); *B05D 5/00* (2013.01); *C03C 17/30* (2013.01); *C03C 17/3405* (2013.01); *C07H 21/04* (2013.01); *B05D 2518/10* (2013.01); *C03C 2217/75* (2013.01)

(58) Field of Classification Search
None
See application file for complete search history.

(56) References Cited

U.S. PATENT DOCUMENTS

2002/0090739 A1* 7/2002 Laguitton ............... C03C 17/30
                                                        436/518
2003/0036062 A1* 2/2003 Bao ..................... G01N 33/54393
                                                         506/39

(Continued)

FOREIGN PATENT DOCUMENTS

WO    WO-2017007753 A1    1/2017

OTHER PUBLICATIONS

Kessler et al. Reactive Surface coatings based on Polysilsesquioxanes: Controlled Functionalization for Specific Protein Immobilization, Langmuir, 2009 vol. 25, p. 10068-10076 (Year: 2009).*

(Continued)

*Primary Examiner* — Cachet I Proctor
(74) *Attorney, Agent, or Firm* — Wilson Sonsini Goodrich & Rosati (57) ABSTRACT

The present disclosure relates to processes for derivatizing a surface of a substrate with a covalently bonded thin film of poly(methylsilsesquioxane)-bonded polymers as a platform for the synthesis of a biomolecule array. These processes can also be used to prepare a surface of a substrate for an in situ solid-phase synthesis of biomolecule array.

20 Claims, 4 Drawing Sheets

(51) Int. Cl.
  *B05D 1/00*    (2006.01)
  *B05D 1/38*    (2006.01)
  *B05D 3/02*    (2006.01)
  *B05D 3/10*    (2006.01)
  *B05D 5/00*    (2006.01)
  *C03C 17/30*   (2006.01)
  *C03C 17/34*   (2006.01)

(56)            References Cited

U.S. PATENT DOCUMENTS

2006/0194252 A1*  8/2006  Hunt ............... B01J 19/0046
                                                         435/7.1
2010/0021954 A1*  1/2010  Deshayes ............ B82Y 30/00
                                                          435/29

OTHER PUBLICATIONS

Sassolads et al. "DNA Biosensors and Microarrays" Chemical Reviews, 2008 vol. 108, pp. 109-139 (Year: 2008).*
International Search Report and Written Opinion in Corresponding PCT Application No. PCT/US2018/021036, dated May 18, 2018.
Kessler et al, "Reactive Surface Coatings based on Polysilsesquioxanes: Controlled Functionalization for Specific Protein Immobilization", Langmuir, 2009, vol. 25, pp. 10068-10076.
Sassolas et al., "DNA Biosensors and Microarrys", Chemical Reviews, 2008, vol. 108, pp. 109-139, Entire Article, more specifically, p. 109, col. 2, para 5.

* cited by examiner

PREPARATION OF UNIVERSAL SPIN-COATABLE AMINE-REACTIVE SURFACE COATINGS FOR BIOMOLECULE ARRAY FABRICATION

CROSS-REFERENCE

This application claims the benefit of U.S. Provisional Patent Application No. 62/472,680, filed on Mar. 17, 2017, which is entirely incorporated herein by reference.

BACKGROUND

Biomolecule arrays with biomolecules immobilized on solid support have been employed in the fields of molecular biology. Biomolecules immobilization may provide advantages, such as, allowing for multiplexing of samples and location addressable identification of signals for target molecules. Creating biomolecule arrays, including oligonucleotide arrays, on a flat solid support, have attracted a lot of research. M. E. Southern et al., *Nucleic Acids Res.* (1994) 22(8):1368-73.

In particular, microarrays (DNA chips) are important tools for high-throughput analysis of biomolecules. One key component for microarray fabrication is the chemistry employed to immobilize DNA probes. Other factors to be considered involve the hydrophilicity of the surface, the accessibility of the surface-bound probes, the density of the probes, and the reproducibility of the underlying chemistry processes. A. Sassolas et al., *Chem. Rev.* (2008) 108(1):109-39. One method to construct oligonucleotide microarrays is the in situ syntheses of oligonucleotides on the chip surface using either photolithographic methods or deposition methods. D. Sethi et al. *Bioconjugate Chem.* (2008) 19(11):2136-43. Self-assembled monolayers have been used to control the lateral spacing of probes on gold surface. K. Kim et al. *Angew, Chem. Int. Ed.* (2003) 42(20):2293-6. Immobilization of DNA by covalent attachment has been reported to rely on functionalized DNA chip surfaces having surface functional groups. S. B. Nimse et al. *Sensors* (2014) 14:22208-29.

Lateral spacing between immobilized oligonucleotides, interference of non-specific binding, and hybridization yield continue to be the problems encountered during the construction of microarrays. Thus, there is a need to search for processes which prepare surfaces of solid supports for biomolecule array fabrication.

SUMMARY

An aspect of the present disclosure provides a solid support, comprising poly(methylsilsesquioxane)-bonded polymers comprising a compound of Formula I:

Formula I wherein linker is -L$^1$-L$^2$-L$^3$-;

L$^1$ and L$^3$, in each occurrence, are independently C$_1$-C$_6$ alkylene or C$_2$-C$_6$ alkoxylene, wherein the C$_1$-C$_6$ alkylene and the C$_2$-C$_6$ alkoxylene are unsubstituted or substituted with 1 to 3 groups selected from the group consisting of C$_1$-C$_3$ alkyl, C$_1$-C$_3$ alkoxy, halide, cyanide and —N(R$^{20}$)—;

L$^2$ is arylene;

R$^1$ is independently selected from the group consisting of:

with the proviso that at least one R$^1$ is

T$^1$ is absent, H, C$_1$-C$_6$ alkyl, or an initiator residue;

X is independently protected or unprotected —OH, protected or unprotected —NHR$^{21}$, protected or unprotected —SH, protected or unprotected —CO$_2$H, protected or unprotected —CHO, protected or unprotected —ONH$_2$, protected or unprotected —NHNH$_2$, —N$_3$, —CCR$^{22}$, or halide;

R$^2$ is independently H, —CH$_3$, or —CH$_2$OCH$_3$;

R$^{20}$, R$^{21}$ and R$^{22}$ are each independently a C$_1$-C$_3$ alkyl;

Capture Probe comprises at least one molecule selected from the group consisting of peptide, protein, glycosylated protein, glycoconjugate, aptomer, carbohydrate, polynucleotide, oligonucleotide and polypeptide;

p is an integer from 2 to 200;
a is an integer from 1 to 5;
b is an integer from 0 to 10;
c is an integer from 1 to 5; and
d is an integer from 0 to 10.

In some embodiments of aspects provided herein, the poly(methylsilsesquioxane) comprises a plurality of repeating units of formula (CH$_3$SiO$_{3/2}$), a set of the plurality of the repeating units of formula (CH$_3$SiO$_{3/2}$) being covalently bonded with the linker of the compound of Formula I.

In some embodiments of aspects provided herein, the Capture Probe is oligonucleotide. In some embodiments of aspects provided herein, the Capture Probe is DNA.

In some embodiments of aspects provided herein, the solid support further comprises a substrate is glass, silica, silicon, fused silica substrates, metal, or polymeric substrate, the substrate being bonded with the poly(methylsilsesquioxane). In some embodiments of aspects provided herein, the substrate is fused silica substrates. In some embodiments of aspects provided herein, the polymeric substrate comprises at least one selected from the group consisting of an acrylnitrile-butadien-styrene, a cyclic olefin polymer, a cyclic olefin copolymer, a polymethylene-methacrylate, a polycarbonate, a polystyrole, a polypropylene, a polyvinylchloride, a polyamide, a polyethylene, a polyethylene-terephthalate, a polytetrafluoro-ethylene, a polyoxymethylene, a thermoplastic elastomer, a thermoplastic polyurethane, a polyimide, a polyether-ether-ketone, a polylactic acid, and a polymethylpentene.

In some embodiments of aspects provided herein, a ratio between the plurality of the repeating units of formula (CH$_3$SiO$_{3/2}$) and the set of the plurality of the repeating units of formula (CH$_3$SiO$_{3/2}$) is from about 15 to about 27. In some embodiments of aspects provided herein, the ratio is from about 18 to about 24. In some embodiments of aspects provided herein, the ratio is from about 20 to about 22.

Another aspect of the present disclosure provides a method of derivatizing a surface of a substrate, comprising:

(a) contacting a surface of a substrate with a first reagent comprising poly(methylsilsesquioxane)-bonded polymers comprising a compound of Formula I:

Formula I wherein linker is -$L^1$-$L^2$-$L^3$-;

$L^1$ and $L^3$, in each occurrence, are independently $C_1$-$C_6$ alkylene or $C_2$-$C_6$ alkoxylene, wherein the $C_1$-$C_6$ alkylene and the $C_2$-$C_6$ alkoxylene are unsubstituted or substituted with 1 to 3 groups selected from the group consisting of $C_1$-$C_3$ alkyl, $C_1$-$C_3$ alkoxy, halide, cyanide and —N($R^{20}$)—;

$L^2$ is arylene;

$R^1$ is pentafluorophenoxy;

$R^{20}$ is a $C_1$-$C_3$ alkyl;

$T^1$ is absent, H, $C_1$-$C_6$ alkyl, or an initiator residue; and p is an integer from 2 to 200; and (b) reacting a first set of $R^1$ in the polymers with a second reagent comprising wherein Capture Probe comprises at least one molecule selected from the group consisting of peptide, protein, glycosylated protein, glycoconjugate, aptomer, carbohydrate, polynucleotide, oligonucleotide and polypeptide;

a is an integer from 1 to 5; and b is an integer from 0 to 10.

In some embodiments of aspects provided herein, the poly(methylsilsesquioxane) comprises a plurality of repeating units of formula ($CH_3SiO_{3/2}$) and a set of the plurality of repeating units of formula ($CH_3SiO_{3/2}$) covalently bonded with the linker of the compound of Formula I.

In some embodiments of aspects provided herein, the method further comprises, prior to (a), drying or cleaning the surface of the substrate, or treating the surface to provide a plurality of hydroxyl groups.

In some embodiments of aspects provided herein, the surface of the substrate comprises a plurality of hydroxyl groups and after (a) a set of the plurality of hydroxyl groups are covalently bonded with the poly(methylsilsesquioxane).

In some embodiments of aspects provided herein, the contacting in (a) is coating or spin-coating.

In some embodiments of aspects provided herein, the method further comprises, prior to (b), annealing the substrate with the first reagent. In some embodiments of aspects provided herein, the annealing is performed at about 130° C. from about 1 to about 3 hours.

In some embodiments of aspects provided herein, the method further comprises, after (b), reacting a second set of $R^1$ in the polymers with a third reagent selected from the group consisting of:

wherein X is independently protected or unprotected —OH, protected or unprotected —$NHR^{21}$, protected or unprotected —SH, protected or unprotected —$CO_2H$, protected or unprotected —CHO, protected or unprotected —$ONH_2$, protected or unprotected —$NHNH_2$, —$N_3$, —C≡$CR^{22}$, or halide;

$R^2$ is independently H, —$CH_3$, or —$CH_2OCH_3$;

$R^{21}$ and $R^{22}$ are independently a $C_1$-$C_3$ alkyl;

a is an integer from 1 to 5;

b is an integer from 0 to 10;

c is an integer from 1 to 5; and d is an integer from 0 to 10.

In some embodiments of aspects provided herein, the substrate is glass, silica, silicon, fused silica substrates, metal, or polymeric substrate comprising at least one selected from the group consisting of an acrylnitrile-butadien-styrene, a cyclic olefin polymer, a cyclic olefin copolymer, a polymethylene-methacrylate, a polycarbonate, a polystyrole, a polypropylene, a polyvinylchloride, a polyamide, a polyethylene, a polyethylene-terephthalate, a polytetrafluoro-ethylene, a polyoxymethylene, a thermoplastic elastomer, a thermoplastic polyurethane, a polyimide, a polyether-ether-ketone, a polylactic acid, and a polymethylpentene. In some embodiments of aspects provided herein, the substrate is fused silica substrates. In some embodiments of aspects provided herein, the substrate is cyclic olefin copolymer or cyclic olefin polymer.

In some embodiments of aspects provided herein, a ratio between the total repeating units of formula ($CH_3SiO_{3/2}$) and the repeating units of formula ($CH_3SiO_{3/2}$) covalently bonded with the linker of the compound of Formula I is from about 15 to about 27.

In some embodiments of aspects provided herein, ratio between the first fraction of the plurality of the repeating units of formula ($CH_3SiO_{3/2}$) and the total of the plurality of the repeating units of formula ($CH_3SiO_{3/2}$) is from about 15 to about 27.

In some embodiments of aspects provided herein, the Capture Probe comprises a first oligonucleotide. In some embodiments of aspects provided herein, the method comprises, after (b), confirming the first oligonucleotide being immobilized on the surface by detecting a hybridization between the first oligonucleotide and a second oligonucleotide comprising a label and a sequence having complementarity with the first oligonucleotide. In some embodiments of aspects provided herein, the label is a fluorophore.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Because there is a need to search for processes which control density of probes on support surface in order to provide access to target molecules for detection, the applicant experimented and discovered the subject matter of the present disclosure. The present disclosure provides a solid substrate having a spin-coatable amine-reactive surface coating for fabrication of biomolecule arrays, including biomolecule arrays, for example, nucleic acid arrays. The surface of the solid substrate, as disclosed in the present disclosure, comprises a spin-coatable amine-reactive surface coating, which acts as both an anchor for probe attachment and a controlling mechanism for probe density. The present disclosure also provides several methods and processes of derivatizing a surface of a solid support to afford spin-coatable amine-reactive surface coatings, enabling attachment of probe arrays on many surface having hydroxyl groups and controlling probe density. The spin-coatable amine-reactive surface coating is a polysilsesquioxane film with embedded amine-reactive functional groups, which reacts with functionalized probes to attach the probes and can further react with quenching reagent to control the density of the probes. Thus, a spin-coatable amine-reactive surface coating provides a platform for the synthesis of a biomolecule array, including a nucleic acid array, a polypeptide array, or an oligonucleotide array. The disclosed spin-coatable amine-reactive surface coating confers advantages of a controllable density of attachment sites for nucleic acid synthesis and a general applicability to any substrate with surface hydroxyl groups.

The concept of lab-on-chip involves the integration of many analytical operations on a miniaturized platform, for example, a micro-total-analysis-system (μTAS). D. J. Harrison et al., *Anal. Chem.* (1992) 64(17):1926-32. These microchip systems include, for example, microfluidic systems, sensors, arrays or biochips, chemical synthesis on-chip, etc. Developments of the lab-on-chip concept in various analytical areas and novel materials have been reported. D. R. Reyes et al., *Anal. Chem.* (2002) 74(12):2623-36; P. A. Auroux et al., *Anal. Chem.* (2002) 74(12):2637-52.

The solid substrate for these microsystem chips, microfluidic chips, microchips, or biochips, are prepared from, for example, glass, silica, silicon, fused silica substrate materials, titanium oxide, aluminum oxide, indium tin oxide (ITO), and various polymeric materials, titanium, gold, other metals, or other suitable materials. Polymeric materials used include, for example, polydimethylsiloxane (PDMS), poly(methyl methacrylate) (PMMA), polycarbonate (PC), polystyrene (PS), polyethyleneterephthalate (PETG), polyvinylchloride (PVC) polyimide (PI), polyolefins, such as poly(methylpentene) (PMP) and Zeonor™, cyclic olefin copolymer such as Topas™, due to their lower cost, compatibility with biomolecules, optical transparency, number of replication strategies and disposability. H. Becker et al., *Talanta* (2002) 56(2):267-87.

Cyclic olefin copolymer (COC) and cyclic olefin polymer (COP) comprise amorphous thermoplastic polymers and have similar structures, with the exception that COPs use a single type of monomer during formulation. Both are notable for their optical clarity, water absorption, and mechanical properties. These polymers are biocompatible and have the lowest autofluorescence among all hard plastics. Because of their good optical properties, COCs and COPs are frequently used microfluidics and microtiter plates. COCs and COPs are resistant to many solvents used in life sciences applications.

Polymer surface can be treated by oxidation processes, for example, oxygen-plasma, oxidizing flame treatment, etc., to generate surface hydroxyl/ketone/carboxylic groups. R. A. Ryntz, *Painting of Plastics*, Fed. Soc. Coat. Tech., Blue Bell, Pa., USA (1994); S. Farris et al., *Polymer* (2010) 51(16): 2591-3605.

With so many solid substrates to choose from for arrays or biochips, there is a need to find a universal composition which, when applied to any substrate surface, provide unified surface density of anchoring sites for later introduction of biomolecule probes. The present disclosure provides a composition of and fabrication methods for such an intermediate layer between the solid substrate and the probes. This intermediate layer takes advantage of surface hydroxyl/carbonyl/carboxylic groups on glass, metal and polymers to form covalent bonds between the intermediate layer and the substrate surface. In addition, the intermediate layer carries functional groups that are amine-reactive for the later introduction of biomolecule probes.

The term "oligonucleotide" as used herein refers to a nucleotide chain. In some cases, an oligonucleotide is less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligonucleotide (e.g., a primer). Oligonucleotides can comprise natural nucleotides, non-natural nucleotides, or combinations thereof.

The term "initiator" as used herein refers to a molecule that is used to initiate a polymerization reaction. Initiators for use in preparation of polymers are well known in the art. Representative initiators include, but are not limited to, initiators useful in atom transfer radical polymerization, living polymerization, the AIBN family of initiators and benzophenone initiators. An "initiator residue" is that portion of an initiator which becomes attached to a polymer through radical or other mechanisms. In some embodiments, initiator residues are attached to the terminal end(s) of the disclosed polymers. In the present disclosure, "initiator" and "initiator residue" can be interchangeable when describing initiator molecules left on a polymeric molecule.

The term "substrate" as used herein refers to a material having a rigid, semi-rigid or gelatinous surface. Typical examples include solid substrate described above, including glass or suitable polymeric materials. In some embodiments of the present disclosure, at least one surface of the substrate will be substantially flat, although in some embodiments it is desirable to physically separate synthesis regions for different polymers with, for example, wells, raised regions, etched trenches, or the like. In some embodiments, the substrate itself contains wells, trenches, flow through regions, etc. which form all or part of the synthesis regions. According to other embodiments, small beads can be provided on the surface, and compounds synthesized thereon optionally can be released upon completion of the synthesis. Examples of surfaces include flow cells, sequencing flow cells, flow channels, microfluidic channels, capillary tubes, piezoelectric surfaces, wells, microwells, microwell arrays, microarrays, chips, wafers, non-magnetic beads, magnetic beads, ferromagnetic beads, paramagnetic beads, superparamagnetic beads, and polymer gels. Substrates are well known in the art and are readily commercially available through vendors such as USPG, PPG Industries, AFG Industries and others. In certain embodiments, the substrates used in the present disclosure are those that are readily silanated, such as glass, quartz, fused silica and silicon wafers. D. Cuschin et al., *Anal. Biochem.* (1997) 250(2):203-11.

As used herein, the singular form "a," "an," and "the" include plural references unless the context clearly dictates otherwise. For example, the term "a reagent" includes a plurality of reagents, including mixtures thereof.

The term "about" as used herein refers to +/−15%, 10%, 9%, 8%, 7%, 6%, 5%, 4%, 3%, 2%, or 1% of the designated amount.

The term "film" as used herein refers to a layer or coating having one or more constituents, applied in a generally uniform manner over the entire surface of a substrate, for example, by spin coating. For example, in accordance with an aspect of the present disclosure, a film is a solution, suspension, dispersion, emulsion, or other acceptable form of a chosen polymer. A film can include additional chemical reagents in combination with a film-forming polymer. Film-forming polymers are polymers, which after melting or dissolving in a compatible solvent can form a uniform film on a substrate. A polymeric film can be covalently bonded to the surface of a substrate via a chemical bond such as, for example, an amide bond, an ester bond, an alkylamino bond, and an alkoxy bond.

The term "reactive group" as used herein refers to a functional group that has reactivity for another target functional group such that the reactive group will react preferentially with the target functional group. For example, an amine-reactive group is a functional group, such as, for example, an activated carbonyl compounds, including esters and amides, which preferentially react with the amine group.

The term "analyte" or "analyte molecule" as used herein refers to a compound or molecule which is the subject of an analysis. For example an analyte molecule can be of unknown structure and the analysis includes identification of the structure. Analyte molecules include any number of common molecules, including DNA, proteins, peptides and carbohydrates, organic and inorganic molecules, metals (including radioactive isotopes), and the like. Analytes include viruses, bacteria, plasmodium, fungi, as well as metals and bio-warfare, bio-hazard and chemical warfare materials. In some embodiments, the analyte are treated to comprise a fluorescent label, such as a fluorophore label or a quencher. The label on the analyte can interact with the label on the probe to indicate the presence or absence of the analyte-probe interactions.

The term "probe" as used herein refers to a molecule used for indirect identification of an analyte molecule. For example, a probe can carry sequence information which uniquely identifies an analyte molecule. Exemplary probes include carbohydrate, oligonucleotides and polypeptide, among others, with or without a linker.

The term "capture probe" as used herein refers to a molecule capable of interacting with an analyte molecule, for example by hydrogen bonding (e.g., DNA hybridization), sequestering, covalent bonding, ionic interactions, and the like. Exemplary capture probes include oligonucleotides which are capable of sequence specific binding (hybridization) with oligonucleotide probes or flaps, oligosaccharides (e.g. lectins) and proteins. In some embodiments capture probes comprise a fluorophore label. For example the capture probe can comprise a fluorophore label and an analyte molecule can comprise a quencher, and the presence of the analyte molecule is detected by an absence of a fluorescent signal from the capture probe (since the fluorescence is quenched upon interaction with the quencher). In related embodiments, the capture probe comprises a quencher. In these embodiments, the fluorescence of a fluorescently labeled analyte molecule is quenched upon capture by the capture probe. Exemplary probes include peptide, protein, glycosylated protein, glycoconjugate, aptomer, carbohydrate, polynucleotide, oligonucleotide and polypeptide.

The term "protected" or "protection" or "protecting group," as used herein regarding chemical groups, refers to forming a covalent bond between a specific chemical group (including, for example, —OH, —NH—, —CO$_2$H, —SH, and —CHO) and another chemical group (protecting group) in such a way as to mask the specific chemical group and/or modify the reactivity of the specific chemical group. In some embodiments, the protecting group can be removed later in the synthetic process to reveal the original, specific chemical group. The protection of chemical groups by protecting groups, the protecting groups themselves, and the removal reactions of protecting groups (commonly referred to as "deprotection") are described in, for example, R. Larock, *Comprehensive Organic Transformations*, VCH Publishers (1989); T. W. Greene and P. G. M. Wuts, *Protective Groups in Organic Synthesis*, 3rd edition, John Wiley and Sons (1999); L. Fieser and M. Fieser, Fieser and Fieser's Reagents for Organic Synthesis, John Wiley and Sons (1994); A. Katritzky and A. Pozharski, *Handbook of Heterocyclic Chemistry*, 2nd edition (2001); M. Bodanszky, A. Bodanszky, *The Practice of Peptide Synthesis*, Springer-Verlag, Berlin Heidelberg (1984); J. Seyden-Penne, *Reductions by the Alumino- and Borohydrides in Organic Synthesis*, 2nd edition, Wiley-VCH, (1997); and L. Paquette, editor, *Encyclopedia of Reagents for Organic Synthesis*, John Wiley and Sons (1995). When synthesizing the compounds of Formulas I-IV described herein, protecting groups can be used to protect specific chemical groups. The term "unprotected" as used herein refers to a specific chemical group or naked chemical group without forming a covalent bond with a protecting group.

The practice of the present disclosure employs techniques of organic chemistry, polymer technology, molecular biology (including recombinant nucleic acid techniques), cell biology, biochemistry, and immunology as would be understood by a person having ordinary skill in the art. Such techniques include hybridization, ligation, and detection of hybridization using a label. Specific illustrations of suitable techniques can be found in the examples disclosed hereinafter. However, other equivalent conventional procedures can be used. Such conventional techniques and descriptions can be found in standard laboratory manuals such as, for example, *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press); Stryer, L. (1995) *Biochemistry* (4th Ed.) Freeman, New York; Gait, "*Oligonucleotide Synthesis: A Practical Approach*" 1984, IRL Press, London; Nelson and Cox (2000), Lehninger, *Principles of Biochemistry* 3rd Ed., W. H. Freeman Pub., New York, N.Y.; Brinker and Scherer (1990), *Sol-Gel Science*, Academic Press, San Diego, Calif.; and Berg et al. (2002) *Biochemistry*, 5th Ed., W. H. Freeman Pub., New York, N.Y., all of which are herein incorporated by reference in their entirety.

Figure 1:
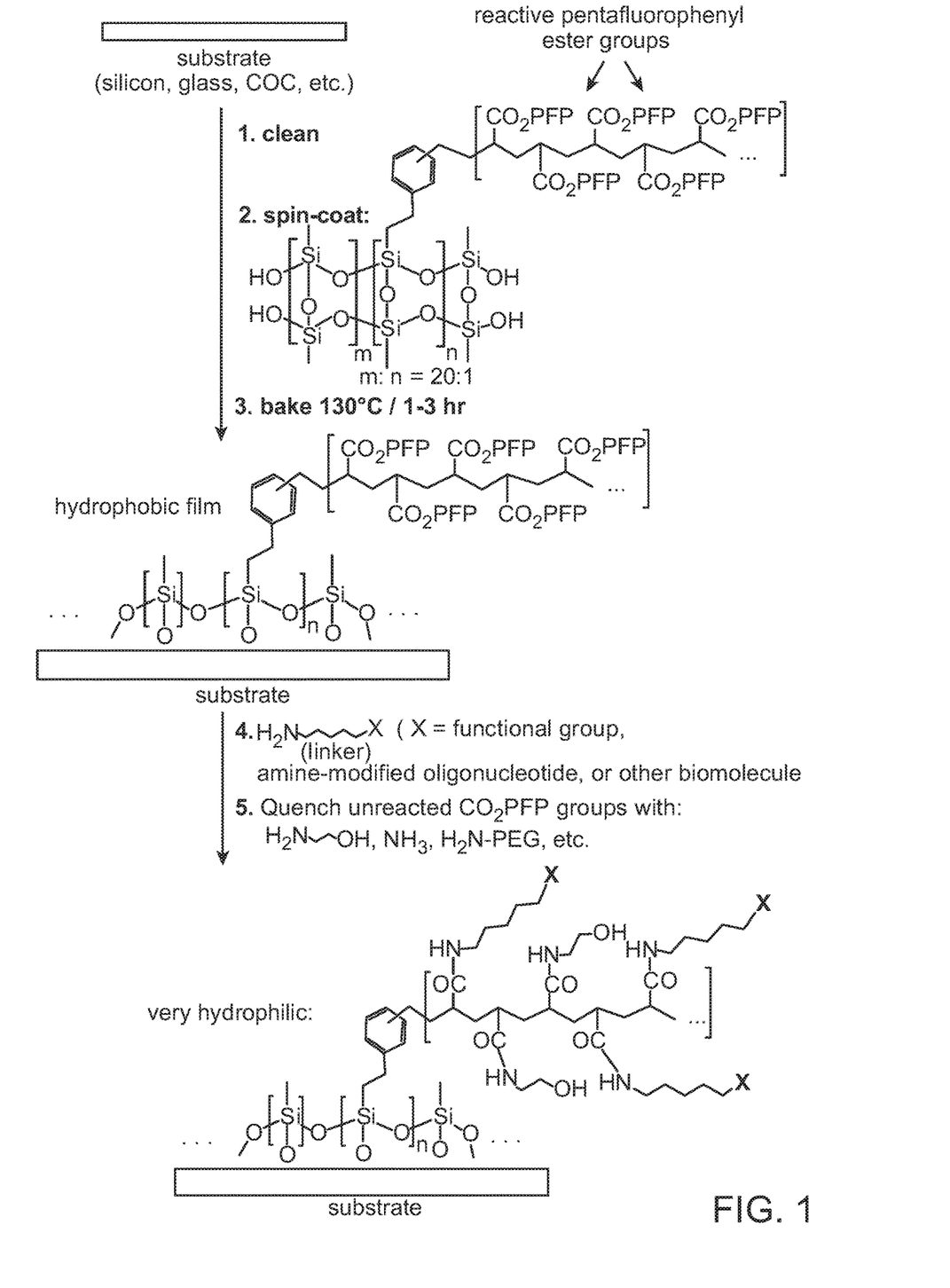
FIG. 1 shows exemplary embodiments of the solid support and preparation thereof according to the present disclosure.

Turning now to FIG. 1, which shows an exemplary embodiment of the solid support and preparation thereof according to the present disclosure. In Step 1, the surface of the substrate is cleaned. The substrate can be any substrate with active groups on the surface. In some embodiments, the active groups are hydroxyl, carbonyl or carboxylic groups. In some embodiments, the active group is preferably hydroxyl groups. In some embodiments, cleaning comprises soaking, agitating, rinsing, washing, drying, or combinations thereof with or without a solvent, at room temperature or elevated temperature, from about 5 minutes to more than 24 hours. In some embodiments, cleaning also comprises surface treatment to introduce active groups on the surface of the substrate, for example, oxygen plasma and oxidizing flame treatment, etc.

After the surface of the substrate is cleaned, in some embodiments, a first reagent, i.e., a polysilsesquioxane reagent, is spin coated onto the surface in Step 2 of FIG. 1. The polysilsesquioxane (PSQ) is a silicon resin synthesized from trifunctional organosilane compounds ($X_3SiR$, X is alkoxy or halide, R is an alkyl or aryl group) and is an organic/inorganic hybrid material that combines the inorganic characteristics presented by the siloxane bond (Si—O—Si), which constitutes the main chain, and the organic characteristics presented by the organic functional group (R) that constitutes the side chain. Various polysilsesquioxane products can be synthesized by using organo-trichlorosilane and/or organo-trialkoxysilane as the raw materials. The organo-moiety of the trifunctional organosilane compounds can be a simple methyl group for the backbone part or a complex functional chain for the biomolecule probe part. In some embodiments, a mixture of trifunctional organosilane compounds with different organo-moieties can be used to provide functionalized PSQ as shown below. In some embodiments, the functionality embedded in PSQ's can be amine-reactive groups, which are covalently bonded to the PSQ via a linker. In some embodiments, the linker has a length from one carbon to twenty carbons, some of which can be replaced by a hetero atom selected from —S—, —O— or —N($R^{20}$)—, wherein $R^{20}$ is a $C_1$-$C_3$ alkyl. In some embodiments, the amine-reactive group can be a pentafluorophenyl (PFP) ester as shown in FIG. 1. Thus, in some embodiments, the first reagent in Step 2 of FIG. 1 can comprise a PSQ-linker-PFP molecule.

In some embodiments, to synthesize the first reagent, for example, PSQ-linker-PFP as shown in FIG. 1, sol-gel chemistry is employed. In some embodiments, two types of trifunctional organosilane compounds are used to synthesize the first reagent. One type is trimethoxy(methyl)silane. The other type is 3-(2-(trimethoxysilyl)ethyl)benzyl benzodithioate or 4-(2-(trimethoxysilyl)ethyl)benzyl benzodithioate or a mixture thereof. In some embodiments, mixing these two types of organosilane compounds in the presence of acid allows acid-catalyzed hydrolytic polycondensation among the organosilane reagents shown in Scheme 1 to give a condensed polymer of Formula II:

Scheme 1

Formula II wherein m is an integer from 0 to 60;

n is an integer of from 1 to 3;

q is an integer of from 0 to 60;

w is an integer of from 2 to 100; and ratio of (m+q)/n is from about 15 to about 25.

It should be point out that although in Formula II, n monomers of the benzyl benzodithioate moiety are shown as consecutive monomers, in some embodiments, the n monomers of the benzyl benzodithioate moiety in Formula II can be non-consecutive as well, within each repeating unit, as is common in co-polymers. In some embodiment, the ratio between the units within the condensed polymer of Formula II is from about 15 to about 25, whether n monomers of the benzyl benzodithioate moiety are consecutive or not.

The benzodithioate moiety is a known chain transfer agent for reversible addition-fragmentation chain transfer (RAFT) reactions which use an addition-fragmentation chain transfer process to afford radical polymerization of monomers, such as acrylates, thereby grafting new polymer chains from the PSQ network. In some embodiments, when a compound of formula II reacts with pentafluorophenyl acrylates in the presence of a radical initiator, for example, AIBN, an amine-reactive compound of Formula III is formed, as shown in Scheme 2:

Scheme 2

Formula II

Formula III wherein $R^1$ is pentafluorophenyloxy;
$T^1$ is absent, H, $C_1$-$C_6$ alkyl, or an initiator residue;
m is an integer of 0-60;
n is an integer of from 1 to 3;
p is an integer of from 2 to 200;
q is an integer of from 0 to 60;
w is an integer of from 2 to 100; and
ratio of (m+q)/n is from about 15 to about 25.

It should be noted that although pentafluorophenyl ester is shown in the amine-reactive compound of Formula III, other reactive esters can be used in the amine-reactive compound of Formula III as well. For example, $R^1$ in Formula III can be anyone from the following:

After the amine-reactive compound of Formula III is formed, it is spin coated onto the cleaned surface with hydroxyl groups in Step 2 of FIG. 1.

In some embodiments, as shown in Step 3 of FIG. 1, the substrate with spin-coated polysilsesquioxane film with grafted amine-reactive compound of Formula III is annealed at elevated temperature, for example at about 130° C. for from about 1 hour to about 3 hours. This thermal treatment can induce further cross-linking of polysilsesquioxane film so that the polysilsesquioxane film is covalently bonded with the surface of the substrate. After annealing, a hydrophobic film of polysilsesquioxane with grafted amine-reactive groups is formed on the surface of the substrates.

In some embodiments, in Step 4, the substrate with a hydrophobic film of cross-linked polysilsesquioxane film grafted with amine-reactive groups is treated with a second reagent to introduce a Capture Probe. The Capture Probe is covalently bonded with an amino group in the second reagent and the amino group can react with the grafted amine-reactive group on the surface of the substrate. In some embodiments, the Capture Probe comprises at least one molecule selected from the croup consisting of peptide, protein, glycosylated protein, glycoconjugate, aptomer, carbohydrate, polynucleotide, oligonucleotide and polypeptide. In some embodiments, the second reagent comprises a primary amino group linked to a functional group, X. The functional group, X, is independently protected or unprotected —OH, protected or unprotected —$NHR^{21}$, protected or unprotected —SH, protected or unprotected —$CO_2H$, protected or unprotected —CHO, protected or unprotected —$ONH_2$, protected or unprotected —$NHNH_2$, —$N_3$, —C≡$CR^{22}$, or halide, wherein $R^{21}$ and $R^{22}$ are each independently a $C_1$-$C_3$ alkyl. These functional groups are the anchor sites to introduce biomolecule probes, including oligonucleotide, protein, polypeptide, etc. The main purpose of the functional groups is to react with a biomolecule of interest to form a covalent bond between the biomolecule and the cross-linked polysilsesquioxane film on the surface of the substrate. As described previously, a protected chemical group refers to covalently bonded chemical group with a suitable protecting group. The suitable protecting group modifies the chemical reactivity of the chemical group and can be removed in a later step to reveal the original chemical group.

In some embodiments, the amount of the second reagent relative to the amount of the grafted amine-reactive group on the surface can be controlled. As a result, the final density/concentration of the Capture Probe bonded to the surface can be controlled, or set at a predetermined level. For example, the final density/concentration of the Capture Probe can be from about 0.1 pmole/cm$^2$ to about 100 nmole/cm$^2$, from about 0.1 pmole/cm$^2$ to about 10 nmole/cm$^2$, from about 0.1 pmole/cm$^2$ to about 1 nmole/cm$^2$, from about 0.1 pmole/cm$^2$ to about 100 pmole/cm$^2$, or from about 1.0 pmole/cm$^2$ to about 10 pmole/cm$^2$. In some embodiments, the density/concentration of the Capture Probe is changed according to the desired ratio of signal to background. As shown in FIG. 1, for all substrates, the final concentration of probes can be modified and controlled both by the concentration of the grafted amine-reactive groups on the surface after the annealing process in Step 3 and by the percentage of these grafted amine-reactive groups which further react with the second reagent bearing the Capture Probe.

Many properties of the support surface can be changed according to the present disclosure. In some embodiments, the solid support of the present disclosure gives opportunities to modify two surface properties. One is the signal-to-noise quality optimized by the probe density/concentration. The other is the hydrophilic or hydrophobic nature of the surface bearing the probe. Increasing the amount of organic polymer fraction relative to the amount of silanol/siloxane fraction would increase hydrophobicity. Increasing the relative amount of silanol/siloxane fraction would increase hydrophilicity. The probes themselves can influence the relative hydrophilic or hydrophobic nature of the surface as well.

In some embodiments, in Step 5, after the grafted amine-reactive groups have reacted with the second reagent in Step 4, the remaining, available amine-reactive groups are treated with a third reagent selected from the group consisting of The third reagent reacts with the remaining amine-reactive groups and deactivates them. The quenching step removes previously unreacted amine-reactive groups which can inter- fere with later detection of target analytes. For example, the remaining unreactive amine-reactive groups may react with target analyte and form a covalent bond with an amino group, or other reactive groups on the target analytes. Such irreversible covalent binding can cause problem for the detection of target analytes near the substrate surface. The addition of the third reagent can modify the relative hydrophilic or hydrophobic nature of the surface by using difference third reagents. For example, by using third reagents with more hetero atoms and/or more hydroxyl groups, the surface hydrophilicity of the solid support can increase.

In some embodiments, after Step 5, the solid support comprises a structure of Formula IV:

Formula IV wherein $R^1$ is independently selected from the group consisting of:

with the proviso that at least one $R^1$ is $T^1$ is absent, H, $C_1$-$C_6$ alkyl, or an initiator residue;
$S^1$ to $S^6$ are each independently, H, part of the surface of the substrate, or a linker to the surface of the substrate;
m is an integer of from 0 to 60;
n is an integer of from 1 to 3;
p is an integer of from 2 to 200;
q is an integer of from 0 to 60;
w is an integer of from 2 to 100; and
ratio of (m+q)/n is from about 15 to about 25.

The amine-active acrylate polymer coatings in Steps 2 and 3 can comprise polymer molecules of a particular length or range of lengths. Polymer molecules can have a length of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 550, 600, 650, 700, 750, 800 backbone atoms or molecules (e.g., carbons). Polymer molecules can have a length of at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 550, 600, 650, 700, 750 monomer units (e.g., acrylate and/or acrylamide molecules).

The grafted amine-reactive group reacts with a second reagent to form an amide bond between the polymer and a linker of the Capture probe in Step 4. In one embodiment, a first fraction of the amine-reactive groups is consumed in Step 4 to form the amide bond linked to the Capture probe and a second fraction of the amine-reactive groups is reacts with a third reagent in Step 5. The ratio between the first and second fractions of the amine-reactive groups can be about 1:100, abut 1:190, about 1:180, about 1:170, about 1:160, about 1:150, about 1:140, about 1:130, about 1:120, about 1:110, about 1:90, about 1:80, about 1:70, about 1:60, about 1:50, about 1:40, about 1:30, about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1; about 8:1, about 9:1, about 10:1, about 11:1, about 12:1, about 13:1, about 14:1, about 15:1, about 16:1, about 17:1, about 18:1, about 19:1, and about 20:1, about 30:1, about 40:1, about 50:1, about 60:1, about 70:1, about 80:1, about 90:1, about 100:1, about 110:1, about 120:1, about 130:1, about 140:1, about 150:1, about 160:1, about 170:1, about 180:1, about 190:1, and about 200:1.

When the Capture Probes are oligonucleotides, the oligonucleotides can comprise primers. The oligonucleotides can comprise cleavable linkages. Cleavable linkages can be enzymatically cleavable. The oligonucleotides can comprise at least 1, 2, 3, 4, 5, 6, 7, 8, 9, 10, 11, 12, 13, 14, 15, 16, 17, 18, 19, 20, 25, 30, 35, 40, 45, 50, 55, or 60 bases. The oligonucleotides can vary in length, such as from 3 to 5 bases, from 1 to 50 bases, from 6 to 12 bases, from 8 to 12 bases, from 15 to 25 bases, from 25 to 35 bases, from 35 to 45 bases, or from 45 to 55 bases. The individual oligonucleotides coupled to the coatings can differ from each other in length or composition.

Biomolecules (e.g., oligonucleotides) can be incorporated into the polymer coatings in a controlled manner, with particular biomolecules located at particular regions of the polymer coatings. Biomolecules can be incorporated into the polymer coatings at random, with particular biomolecules randomly distributed throughout the polymer coatings.

In some embodiments, a composition of the invention comprises a surface of a substrate, a spin-coated polysilsesquioxane film on the surface with grafted polymeric compounds; and at least one oligonucleotide coupled to the polysilsesquioxane film coating with grafted polymeric compounds on the surface of the substrate. In other instances, the surface of the substrate includes at least 1, 10, 100, 10,000, 100,000, 1,000,000, 10,000,000, 100,000,000, or 1,000,000,000 oligonucleotides coupled to the polysilsesquioxane film coating with grafted polymeric compounds.

The polysilsesquioxane film coatings with grafted polymeric compounds described in this disclosure can be robust. The robustness of the polysilsesquioxane film coatings with grafted polymeric compounds can be exhibited by the durability, the resistance to degradation, or the level of attachment of the coating after being subjected to certain conditions. The robustness of the polysilsesquioxane film coatings with grafted polymeric compounds can be exhibited by the number or percentage of biomolecules (e.g., oligonucleotides) molecules coupled to the polysilsesquioxane film coating which remain coupled to the polysilsesquioxane film coating after being subjected to certain conditions. Conditions can include but are not limited to duration of time, a temperature or set of temperatures, presence of chemicals (e.g., acids, bases, reducing agents, oxidizing agents), mechanical forces (e.g. stress, strain, vibrations, high pressures, vacuums), combinations of conditions, or repeated cycles of conditions or combinations of conditions (e.g. reaction cycles comprising temperatures and use of chemicals). Durations of time can comprise at least 1, 2, 3, 4, 5, 6, 7, 8, 9, 10, 20, 30, 40, or 50 minutes, at least 1, 2, 3, 4, 5, 6, 7, 8, 9, 10, 11, 12, 13, 14, 15, 16, 17, 18, 19, 20, 21, 22, or 23 hours, at least 1, 2, 3, 4, 5, 6, 7, 8, 9, 10, 11, 12, or 13 days, or at least 2, 3, 4, 5, 6, 7, 8, 9, 10, 12, 14, 16, 18, 20, 22, 24, 26, 28, 30, 40, 50, or 60 weeks. Temperatures can comprise at most 0, 5, 10, 15, 20, 25, 30, 35, 40, 45, 50, 55, 60, 65, 70, 75, 80, 85, 90, 95, 100, 105, 110, 115, 120, 125, or 130° C. Chemicals can comprise strong acids, weak acids, strong bases, weak bases, strong oxidizers, weak oxidizers, strong reducers, weak reducers, enzymes, monomers, polymers, buffers, solvents, or other reagents. Cycles of conditions can comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 125, 150, 175, 200, 250, 300, 350, 400, 450, 500, 600, 700, 800, 900, 1000, 2000, 3000, 4000, 5000, 6000, 7000, 8000, 9000, or 10,000 cycles. In some embodiments, the polymer coatings herein are used to perform at least 10, 20, 30, 40, 50, 60, 70, 80, 90, 100, 200, 300, 400, 500, 600, 700, 800, 900, or 1000 cycles of conditions, and wherein at least 50, 60, 70, 80, 90, 91, 92, 93, 94, 95, 96, 97, 98, 99, 99.5 or 99.9% the polymer chains remain completely intact and bonded to said surface after the cycles.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

Example 1

Preparation of Chain Transfer Agent (Compound 1)

Compound 1

To a solution of phenyl magnesium bromide (32 mmol; 32 ml of 1.0 M in THF) in a 250 mL round-bottomed flask equipped with reflux condenser under $N_2$ was added carbon disulfide (50 mmol; 3.83 g; 3.0 ml) dropwise over about 5 min, while stirring. Near the end of the addition, a rapid exothermic reaction caused the solution to boil spontaneously for about 10-15 s. The resulting dark orange-red solution was left stirring at room temp in dark under $N_2$ overnight. On the next day 32 mmol (8.80 g; 8.1 ml) of a mixture of (chloromethyl)phenylethyl)trimethoxysilane (mixture of o- and p-isomers; commercially available from Gelest, SIC2295.5) was added dropwise over about 20 min. The solution was warmed to 50° C. and stirred for 3 h. Then the reaction mixture was poured into 150 ml of ice-water mixture and the mixture was extracted with 150 ml diethyl ether. The combined extracts were washed with water (3×), dried over anhydrous MgSO₄, filtered. The filtrate was concentrated to give the product 3/4-(2-trimethoxysilanyl-ethyl)benzyl dithiobenzoate (Compound 1) as an orange-read liquid (10.7 g, 85% yield).

Example 2

Synthesis of Polysilsesquioxane (Compound 2)

Compound 1

Compound 2

Compound 1 (1.25 mmol, 0.500 g) and MeSi(OMe)$_3$ (25 mmol, 3.40 g, 3.56 ml) in THF (25 mL) were added to a 100 mL flask and cooled with ice-water bath. While stirring, water (250 mmol, 4.5 ml) was added, followed by HCl (0.82 mmol, 67 µL). Stirring was continued at 0-4° C. for 3 hrs. The mixture was diluted with ether (75 ml), washed water (40 mL, 2×), mixture of brine and 20×SSC buffer (40 mL, v/v=3:1, 1×), dried over anhydrous MgSO$_4$, then filtered into an evaporating flask. The filtered solution was left at room temperature overnight, then concentrated on rotovap (28 mm Hg/40° C.) to give the product of poly(methyl-co-2-((3/4-dithiobenzoylmethyl)phenyl)ethyl)silsesquioxane) (Compound 2) as an orange-red oil (about 80% yield). Compound 2 is soluble in dioxane, THF, acetone, DCM, but is insoluble in hexane or CCl$_4$. For storage, Compound 2 is dissolved immediately after evaporation in 11.5 mL dry dioxane to give a stable homogeneous solution (~100 mg/ml final concentration) which is stored.

Experiment 3

Synthesis of Polysilsesquioxane Grafted with Poly(pentafluorophenyl acrylate) (Compound 3)

Compound 2

Compound 3

Compound 2 (0.043 mmol, 125 mg in 1.25 mL dioxane), pentafluorophenyl acrylate (2.1 mmol, 500 mg), and azobisisobutyronitrile (AIBN) (0.015 mmol, 2.5 mg) were added to about 4 mL of dioxane with stirring. The solution was degassed (6×, pump-purge $N_2$) to give a homogeneous solution which was heated under $N_2$ at 80° C. for 4 hrs. After cooled to room temperature, hexane (10 mL) was added dropwise to the reaction mixture with vigorous stirring to afford crude poly(methyl-co-2-((3/4-dithiobenzoylmethyl) phenyl)ethyl) silsesquioxane) graft poly(pentafluorophenyl acrylate) (Compound 3) as a light orange solid. Ten minutes after the addition was complete, the solvent was decanted and the solids were rinsed with hexane (1×). Solids were collected, re-dissolved in dioxane (1.0 mL), and then re-precipitated with hexane (10 mL). The solvent was decanted and the solids were collected via filtration, dried under high vacuum to afford the purified Compound 2 as pale orange glass (about 0.34 g). Compound 3 thus obtained was stored in about 2.5 mL dioxane.

Experiment 4

Cleaning Fused Silica Substrates (from ESCO Products Inc.)

Fused silica substrates (ESCO, 2"×3"×0.03") were cleaned by soaking/agitating in Nanostrip (Cyantek, Fremont, Calif.) for 4 hrs. Fused silica substrates were then rinsed thoroughly with deionized water and spin-dried for 5 minutes under a stream of $N_2$ at 35° C. The freshly cleaned substrates were stored under $N_2$ and were coated (as shown below in Experiment 5) within 24 hours.

Experiment 5

Immobilization of Oligonucleotide on Polysilsesquioxane-Coated Fused Silica Substrate Step 1: Substrate Coating
Compound 3 (300 mg) was dissolved in 1.2 mL dioxane, and applied to cleaned fused silica substrate obtained in Experiment 4 by puddling and spinning for 15 s at 4,000 rpm. The coated fused silica substrate was baked at 130° C. for 3 hours.

Step 2: Preparation of Oligonucleotide Primer Solution
A first primer solution ("SSPE") was made by adding 5'-Amino-"Comp SP2" Oligo Primer (10 µL, 1 mM primer stock solution, available from Integrated DNA Technologies, Iowa (IDT)) into 40 µL of 6×SSPE at pH 9.

A second primer solution ("Borate") was made by adding 5'-Amino-"Comp SP2" Oligo Primer (10 µL, 1 mM primer stock solution, available from IDT) into 40 µL of sodium borate buffer (10 mM) at pH 8.5.

Figure 2:
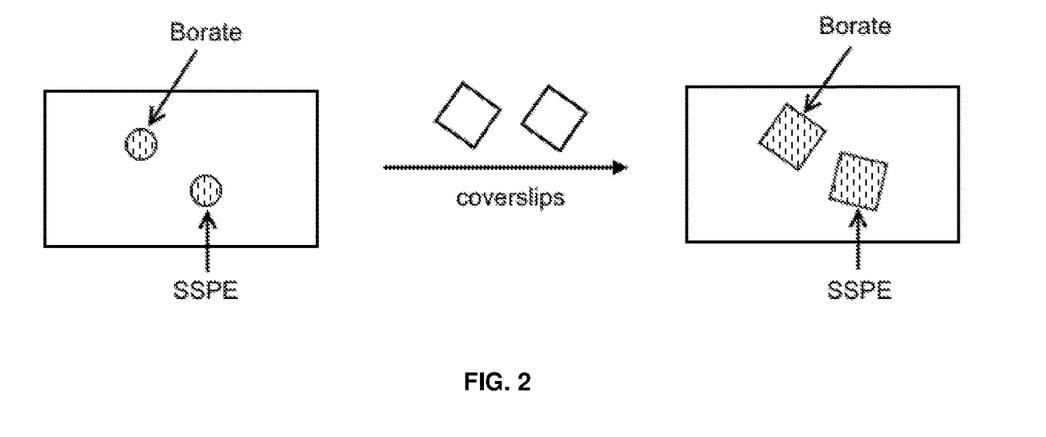
FIG. 2 illustrates an exemplary embodiment of immobilization of oligonucleotide on polysilsesquioxane-coated fused silica substrate in Experiment 5.

Step 3: Substrate Coupling
The first primer solution (20 µL, SSPE) was spotted onto a first location (FIG. 2, left panel) on the Compound 3-coated fused silica substrate, and was spread under a coverslip (22×22 mm) as shown in FIG. 2, right panel The second primer solution (20 µL, Borate) was spotted onto a second location (FIG. 2, left panel) on the same Compound 3-coated fused silica substrate, and was spread under a coverslip (22×22 mm) as shown in FIG. 2, right panel.

Then the primer-treated fused silica substrate was placed in humidified, closed slide holder and left at room temperature overnight for at least 16 hrs in the dark. On the next day, solution under the Borate coverslip had evaporated. After the coverslips were removed, the primer-treated fused silica substrate was rinsed with water and blow dried.

Step 4: Quenching Surface Amine-Reactive Groups with Ethanolamine
The primer-treated fused silica substrate obtained in Step 3 above was placed in a solution of ethanolamine (10% v/v in ethanol) in a container. The container was placed on a shaker and was shaken at room temp for 2 hrs. Then the primer-treated and quenched fused silica substrate was rinsed extensively with water and blow-dried.

Experiment 6

Hybridization with CY3-QC-SP2 Complementary Target Oligonucleotide

A hybridization solution of CY3-QC-SP2 complementary target oligonucleotide (5'-GTGACTGGAGTTCAGACG TGT GCT CTT CCG ATCT-3', available from IDT) is prepared by adding 250 µL of the CY3-QC-SP2 complementary target oligonucleotide (IDT) in 4×SSC (1.0 mL) at pH 7. The primer-treated and quenched fused silica substrate was immersed in the hybridization solution prepared above in a container. The container was placed on a shaker in an oven maintained at 45° C. for 2.5 hrs. After the target-treated fused silica substrate was cooled to room temperature, it was rinsed with 6×SSPE.

Figure 3:
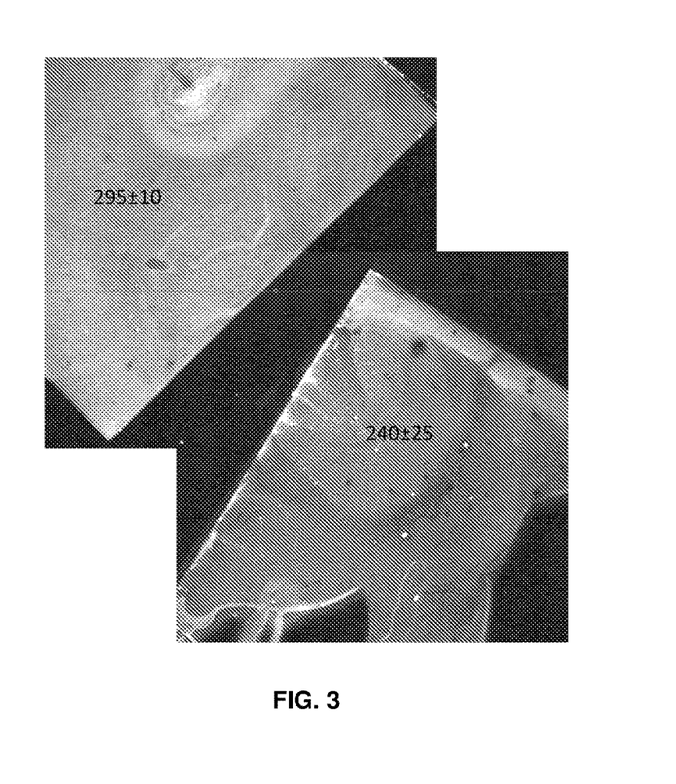
FIG. 3 shows a hybridization image using the fused substrate prepared according to FIG. 2 and treated with CY3-labelled target oligonucleotide.

The hybridized CY3-labeled target in 6×SSPE on the fused silica substrate was placed under a coverslip and imaged under microscope. The acquired image is shown in FIG. 3. The images showed high signal/low background hybridization images for both Borate and SSPE samples on fused silica substrate.

Experiment 7

Stability Test of Probes on Fused Silica Substrate

Figure 4:
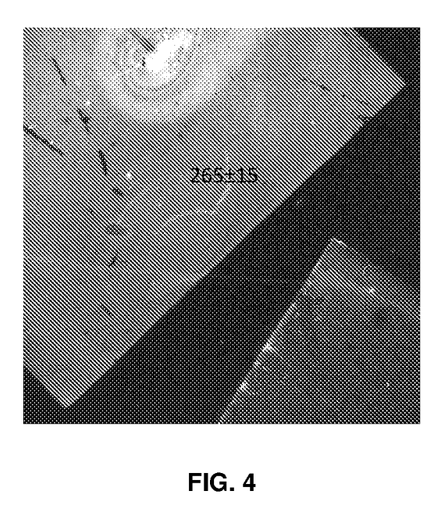
FIG. 4 illustrates a hybridization image of the fused silica substrate, which was used in FIG. 3, rinsed, and further treated with CY3-labelled target oligonucleotide for a stability test.

Substrates were immersed in 6×SSPE buffer at pH 7 and incubated overnight at 50° C. (12 hr). The substrate was rinsed, and then re-hybridized with 100 nM CY3-QC-SP2 complementary target oligonucleotide (from IDT) in 6×SSPE hybridization buffer, similarly to what has been described in Experiment 6. The substrate was immersed in the hybridization solution in a container. The container was placed on a shaker in an oven maintained at 55° C. for 2.0 hrs. After the target-treated fused silica substrate was cooled to room temperature in 0.5 h, it was rinsed with 6×SSPE. The hybridization sample was imaged under microscope to provide an image in FIG. 4. The same high signal/low background hybridization image was maintained. However, the signals displayed lower intensities when compared with the image in FIG. 3.

Experiment 8

Cleaning ZEONOR® Cyclic Olefin Polymer Substrate

ZEONOR® cyclic olefin polymer ("COP") substrate was washed with isopropanol, dried and then treated with $O_2$-plasma (Harrick Plasma, medium power for 30 s; then high power for 15 s.).

Experiment 9

Figure 5:
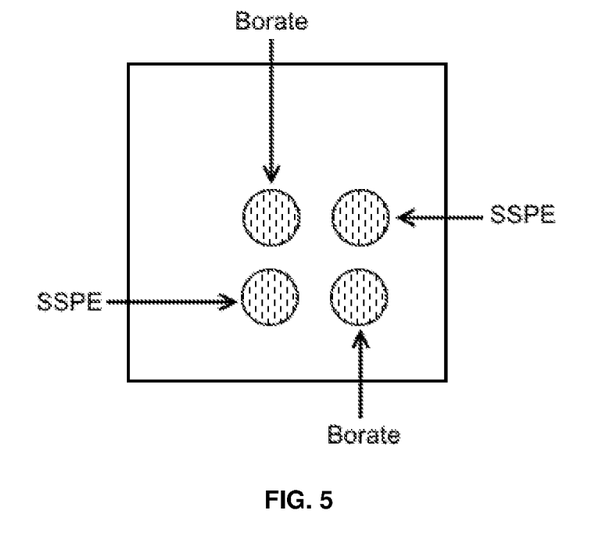
FIG. 5 shows an exemplary embodiment of immobilization of oligonucleotide on cyclic olefin polymer (COP) substrate in Experiment 9.

Immobilization of Oligonucleotide on Polysilsesquioxane-Coated COP Substrate Step 1: Substrate Coating
The procedure was similar to that in Step 1 of Experiment 5.
Step 2: Preparation of Oligonucleotide Primer Solution
The procedure was similar to that in Step 2 of Experiment 5.
Step 3: Substrate Coupling
The first primer solution (5 μL, SSPE) was spotted onto two diagonal locations (FIG. 5) on the Compound 3-coated COP substrate
The second primer solution (5 μL, Borate) was spotted onto two different diagonal locations (FIG. 5) on the same Compound 3-coated COP substrate.
Then the primer-treated COP substrate was placed in humidified, closed slide holder and left at room temperature overnight for at least 16 hrs in the dark. On the next day, solution for the first primer (Borate) had evaporated. The primer-treated COP substrate was rinsed with water and blow dried. All four spots on the COP substrate were very hydrophilic.
Step 4: Quenching Surface Amine-Reactive Groups with Ethanolamine
The procedure was similar to that in Step 4 of Experiment 5.

Experiment 10

Hybridization with CY3-QC-SP2 Complementary Target Oligonucleotide

Figure 6:
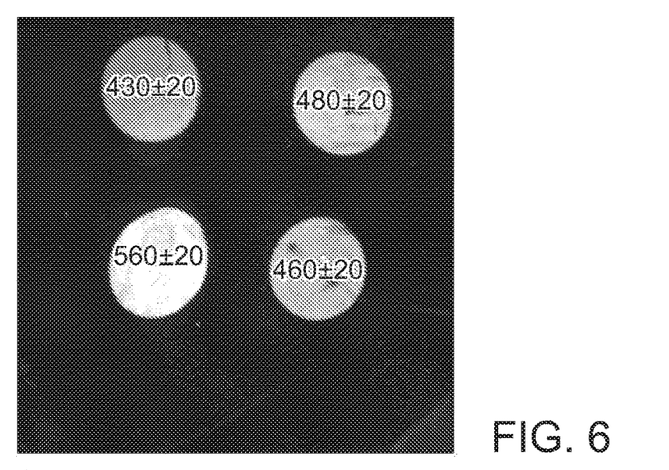
FIG. 6 illustrates a hybridization image using the COP substrate prepared according to FIG. 5 and treated with CY3-labelled target oligonucleotide.

The procedure was similar to that in Experiment 6 for the hybridization.
The hybridized CY3-labeled target in 6×SSPE on COP substrate was placed under a coverslip and imaged under microscope. The acquired image is shown in FIG. 6. The images showed high signal/low background hybridization images for both Borate and SSPE samples on fused silica substrate.

Experiment 11

Stability Test of Probes on COP Substrate

Figure 7:
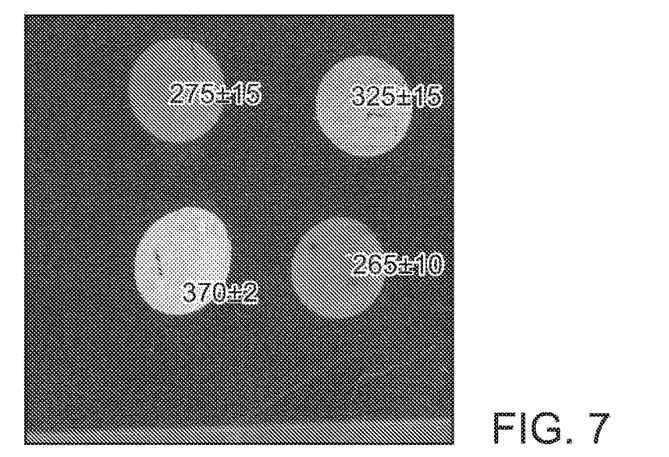
FIG. 7 shows a hybridization image of the COP substrate, which was used in FIG. 6, rinsed, and further treated with CY3-labelled target oligonucleotide for a stability test.

The procedure was similar to that in Experiment 7 for the stability test. The hybridization sample was imaged under microscope to provide an image in FIG. 7. The same high signal/low background hybridization image was maintained. However, the signals displayed lower intensities when compared with the image in FIG. 6.

Experiment 12

Hybridization with Higher Target Concentration

Figure 8:
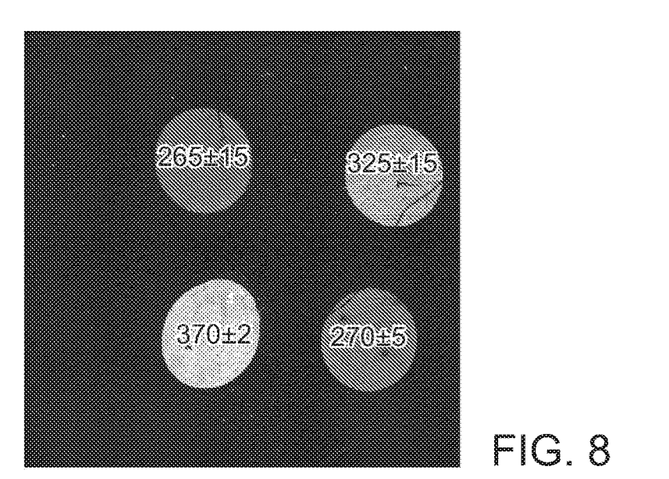
FIG. 8 illustrates shows a hybridization image of the COP substrate, which was used in FIG. 7, rinsed, and further treated with CY3-labelled target oligonucleotide (250 nM) for a stability test.

To check if lower intensities observed in Experiment 11 was due to lower target concentrations in the hybridization solution, the COC substrate from Experiment 11 was rinsed with DI water, then was re-hybridized with 250 nM CY3-QC-SP2 complementary target oligonucleotide in 4×SSE as described in Experiment 6. The container was placed on a shaker in an oven maintained at 55° C. for 2.0 hrs. After the target-treated fused silica substrate was cooled to room temperature in 0.5 h, it was rinsed with 6×SSPE. The hybridization sample was imaged under microscope to provide an image in FIG. 8. Almost identical readings were obtained in FIGS. 7 and 8 for each spot with covalently attached probes. Accordingly, since a higher concentration (250 nM vs. 100 nM) did not increase the observed intensity of hybridized target, the lower concentration (100 nM) of targets already saturated the available probes on the COP substrate for hybridization purposes.

Advantages

Comparing images in FIGS. 2-8 demonstrated that the polysilsesquioxane-coated substrates of the present disclosure exhibited the following characteristics:
The polysilsesquioxane surface coatings according to the present disclosure are universally applicable to many different substrate surfaces;
The polysilsesquioxane surface coatings according to the present disclosure can be applied to, and adhere to thereafter, a variety of inorganic substrates or organic polymer substrates.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:
1. A solid support, comprising poly(methylsilsesquioxane)-bonded polymers comprising a compound of Formula I:

Formula I wherein linker is -$L^1$-$L^2$-$L^3$-;
$L^1$ and $L^3$, in each occurrence, are independently $C_1$-$C_6$ alkylene or $C_2$-$C_6$ alkoxylene, wherein the $C_1$-$C_6$ alkylene and the $C_2$-$C_6$ alkoxylene are unsubstituted or substituted with 1 to 3 groups selected from the group consisting of $C_1$-$C_3$ alkyl, $C_1$-$C_3$ alkoxy, halide, cyanide and —N($R^{20}$)—;
$L^2$ is arylene;
$R^1$ is independently selected from the group consisting of:

-continued with the proviso that at least one $R^1$ is $T^1$ is absent, H, $C_1$-$C_6$ alkyl, or an initiator residue;
X is independently protected or unprotected —OH, protected or unprotected —$NHR^{21}$, protected or unprotected —SH, protected or unprotected —$CO_2H$, protected or unprotected —CHO, protected or unprotected —$ONH_2$, protected or unprotected —$NHNH_2$, —$N_3$, —C≡$CR^{22}$, or halide;
$R^2$ is independently H, —$CH_3$, or —$CH_2OCH_3$;
$R^{20}$, $R^{21}$ and $R^{22}$ are each independently a $C_1$-$C_3$ alkyl;
Capture Probe comprises at least one molecule selected from the group consisting of peptide, protein, glycosylated protein, glycoconjugate, aptomer, carbohydrate, polynucleotide, oligonucleotide and polypeptide;
p is an integer from 2 to 200;
a is an integer from 1 to 5;
b is an integer from 0 to 10;
c is an integer from 1 to 5; and
d is an integer from 0 to 10.

2. The solid support of claim 1, wherein the poly(methylsilsesquioxane) comprises a plurality of repeating units of formula ($CH_3SiO_{3/2}$), a set of the plurality of the repeating units of formula ($CH_3SiO_{3/2}$) being covalently bonded with the linker of the compound of Formula I.

3. The solid support of claim 1, wherein the Capture Probe is oligonucleotide.

4. The solid support of claim 3, wherein the Capture Probe is DNA.

5. The solid support of claim 1, further comprising a substrate of glass, silica, silicon, fused silica substrates, metal, or polymeric substrate, the substrate being bonded with the poly(methylsilsesquioxane).

6. The solid support of claim 5, wherein the substrate is fused silica substrates.

7. The solid support of claim 5, wherein the polymeric substrate comprises at least one selected from the group consisting of an acrylnitrile-butadien-styrene, a cyclic olefin polymer, a cyclic olefin copolymer, a polymethylene-methacrylate, a polycarbonate, a polystyrole, a polypropylene, a polyvinylchloride, a polyamide, a polyethylene, a polyethylene-terephthalate, a polytetrafluoro-ethylene, a polyoxymethylene, a thermoplastic elastomer, a thermoplastic polyurethane, a polyimide, a polyether-ether-ketone, a polylactic acid, and a polymethylpentene.

8. The solid support of claim 2, wherein a ratio between the plurality of the repeating units of formula ($CH_3SiO_{3/2}$) and the set of the plurality of the repeating units of formula ($CH_3SiO_{3/2}$) is from about 15 to about 27.

9. A method of derivatizing a surface of a substrate, comprising:
(a) contacting a surface of a substrate with a first reagent comprising poly(methylsilsesquioxane)-bonded polymers comprising a compound of Formula I:

Formula I wherein linker is -$L^1$-$L^2$-$L^3$-;
$L^1$ and $L^3$, in each occurrence, are independently $C_1$-$C_6$ alkylene or $C_2$-$C_6$ alkoxylene, wherein the $C_1$-$C_6$ alkylene and the $C_2$-$C_6$ alkoxylene are unsubstituted or substituted with 1 to 3 groups selected from the group consisting of $C_1$-$C_3$ alkyl, $C_1$-$C_3$ alkoxy, halide, cyanide and —$N(R^{20})$—;
$L^2$ is arylene;
$R^1$ is pentafluorophenoxy;
$R^{20}$ is a $C_1$-$C_3$ alkyl;
$T^1$ is absent, H, $C_1$-$C_6$ alkyl, or an initiator residue; and
p is an integer from 2 to 200; and
(b) reacting a first set of $R^1$ in the polymers with a second reagent comprising wherein Capture Probe comprises at least one molecule selected from the group consisting of peptide, protein, glycosylated protein, glycoconjugate, aptomer, carbohydrate, polynucleotide, oligonucleotide and polypeptide;
a is an integer from 1 to 5; and
b is an integer from 0 to 10.

10. The method of claim 9, wherein the poly(methylsilsesquioxane) comprises a plurality of repeating units of formula ($CH_3SiO_{3/2}$) and a set of the plurality of repeating units of formula ($CH_3SiO_{3/2}$) covalently bonded with the linker of the compound of Formula I.

11. The method of claim 9, further comprising, prior to (a), drying or cleaning the surface of the substrate, or treating the surface to provide a plurality of hydroxyl groups.

12. The method of claim 9, wherein the surface of the substrate comprises a plurality of hydroxyl groups and after (a) a set of the plurality of hydroxyl groups are covalently bonded with the poly(methylsilsesquioxane).

13. The method of claim 9, wherein contacting in (a) is coating or spin-coating.

14. The method of claim 9, further comprising, prior to (b), annealing the substrate with the first reagent.

15. The method of claim 14, wherein the annealing is performed at about 130° C. from about 1 to about 3 hours.

16. The method of claim 9, further comprising, after (b), reacting a second set of $R^1$ in the polymers with a third reagent selected from the group consisting of:

wherein X is independently protected or unprotected —OH, protected or unprotected —$NHR^{21}$, protected or unprotected —SH, protected or unprotected —$CO_2H$, protected or unprotected —CHO, protected or unprotected —ONH$_2$, protected or unprotected —NHNH$_2$, —N$_3$, —C≡CR$^{22}$, or halide;

R$^2$ is independently H, —CH$_3$, or —CH$_2$OCH$_3$;

R$^{21}$ and R$^{22}$ are independently a C$_1$-C$_3$ alkyl;

a is an integer from 1 to 5;

b is an integer from 0 to 10;

c is an integer from 1 to 5; and d is an integer from 0 to 10.

17. The method of claim 9, wherein the substrate is glass, silica, silicon, fused silica substrates, metal, or polymeric substrate comprising at least one selected from the group consisting of an acrylnitrile-butadien-styrene, a cyclic olefin polymer, a cyclic olefin copolymer, a polymethylene-methacrylate, a polycarbonate, a polystyrole, a polypropylene, a polyvinylchloride, a polyamide, a polyethylene, a polyethylene-terephthalate, a polytetrafluoro-ethylene, a polyoxymethylene, a thermoplastic elastomer, a thermoplastic polyurethane, a polyimide, a polyether-ether-ketone, a polylactic acid, and a polymethylpentene.

18. The method of claim 9, wherein a ratio between the total repeating units of formula (CH$_3$SiO$_{3/2}$) and the repeating units of formula (CH$_3$SiO$_{3/2}$) covalently bonded with the linker of the compound of Formula I is from about 15 to about 27.

19. The method of claim 9, wherein the Capture Probe comprises a first oligonucleotide.

20. The method of claim 19, further comprising, after (b), confirming the first oligonucleotide being immobilized on the surface by detecting a hybridization between the first oligonucleotide and a second oligonucleotide comprising a label and a sequence having complementarity with the first oligonucleotide.

* * * * *